(12) United States Patent
Stewart et al.

(10) Patent No.: US 8,350,114 B2
(45) Date of Patent: Jan. 8, 2013

(54) SEPARATION SYSTEM AND METHOD

(75) Inventors: Douglas G. Stewart, Wheeling, IL (US); Grace Chao, Carpentersville, IL (US); Braden E. Smith, Downers Grove, IL (US); Stephen W. Sohn, Arlington Heights, IL (US); Robert J. L. Noe, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/331,614

(22) Filed: Dec. 20, 2011

(65) Prior Publication Data

US 2012/0090731 A1   Apr. 19, 2012

Related U.S. Application Data

(62) Division of application No. 12/412,482, filed on Mar. 27, 2009.

(51) Int. Cl.
*C07C 7/12* (2006.01)

(52) U.S. Cl. .................................. 585/820; 585/825

(58) Field of Classification Search .................. None
See application file for complete search history.

(56) References Cited

U.S. PATENT DOCUMENTS

| 40,006 A | * | 9/1863 | Keefer et al. .............. 417/539 |
| 2008/0149565 A1 | * | 6/2008 | Lee et al. .................. 210/663 |

* cited by examiner

*Primary Examiner* — Tam M Nguyen
(74) *Attorney, Agent, or Firm* — Arthur E Gooding

(57) ABSTRACT

One exemplary embodiment can be a separation system. The separation system can include an adsorption zone, a rotary valve, a transition zone, and one or more pipes. Usually, the transition zone includes one or more lines communicating the rotary valve with the adsorption zone. The rotary valve alternatively may distribute an input of a feed or a desorbent to the adsorption zone or alternatively can receive an output of a raffinate or an extract from the adsorption zone in a line, and a remnant may remain in the line from a previous input or output. One or more pipes outside the transition zone communicating with the rotary valve can form at least one pipe volume receiving an input for dislodging a remnant or for receiving a remnant from the line. The remnant may be different from the input or output.

3 Claims, 1 Drawing Sheet

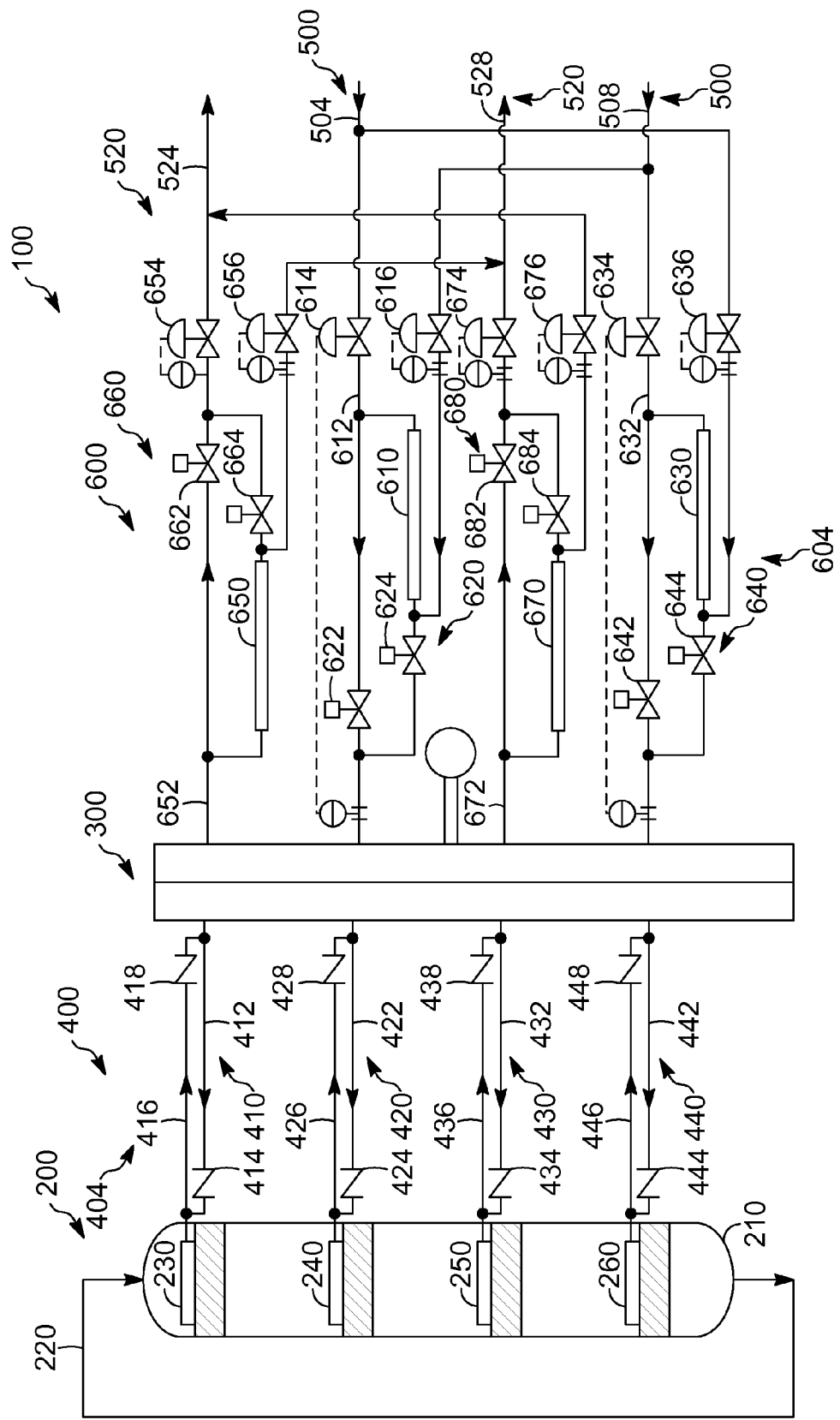

SEPARATION SYSTEM AND METHOD

CROSS-REFERENCE TO RELATED APPLICATION

This application is a Division of prior copending application Ser. No. 12/412,482 which was filed Mar. 27, 2009, the contents of which are incorporated herein by reference thereto.

FIELD OF THE INVENTION

This invention generally relates to a separation system for separating a desired component from one or more other components in a stream.

DESCRIPTION OF THE RELATED ART

Adsorptive separation can be used to purify a hydrocarbon stream by selecting a single compound from one or more other compounds in a stream. Generally, it is desirable to obtain the highest possible purity of the adsorbed compound. As a consequence, usually minimizing contamination of the product is preferable.

In technology such as a simulated moving bed, typically two streams are provided to the bed, namely a feed and a desorbent, and two streams are withdrawn from the bed, namely a raffinate and an extract. Impurities can occur when supplying and removing these various streams to the bed because often the same lines are utilized to provide the feed and desorbent as well as withdrawing the raffinate and extract. As a consequence, the next stream in the series can contain remnants from an earlier stream, and thus degrade operations and/or product purity. As a consequence, it would be desirable to provide an adsorptive separation system that minimizes the contaminants and enhances operations and product purity.

SUMMARY OF THE INVENTION

One exemplary embodiment can be a separation system. The separation system can include an adsorption zone, a rotary valve, a transition zone, and one or more pipes. Usually, the transition zone includes one or more lines communicating the rotary valve with the adsorption zone. The rotary valve alternatively may distribute an input of a feed or a desorbent to the adsorption zone, or alternatively can receive an output of a raffinate or an extract from the adsorption zone in a line, and a remnant may remain in the line from a previous input or output. One or more pipes outside the transition zone communicating with the rotary valve can form at least one pipe volume receiving an input for dislodging a remnant or for receiving a remnant from the line. The remnant may be different from the input or output.

Another exemplary embodiment can be a separation system for separating a desired component from one or more other components in a stream. The separation system can include an adsorption zone, a rotary valve, and a transition zone. The transition zone can include a plurality of lines communicating the rotary valve with the adsorption zone. The plurality of lines may be segregated into pairs with one line adapted to bring an input to the adsorption zone, and the other line adapted to receive an output from the adsorption zone, and each line of the pair contains a respective check valve.

A further exemplary embodiment may include a method of minimizing cross-contamination of fluids in a simulated moving bed. The method can include filling a replacement volume on one side of a valve corresponding to a volume in a line on the other side of the valve to either dislodge a remnant in the line from a previous input, or receive a remnant in the line from a previous output. Generally, the previous input or output is different from the current input or output.

As disclosed herein, the embodiments can provide a system and method for minimizing contamination of various streams sent and received from an adsorptive bed. Particularly, the embodiments disclosed herein are particularly applicable to a simulated moving bed technology where contamination of the various streams can be avoided. As an example, avoiding contamination can improve the extraction of the desired component from a feed as well as minimizing contamination of a final product. Providing at least one pipe volume acting as a receptacle for an output of a raffinate or an extract, or an input that can displace a remnant of a feed or desorbent in a line can facilitate the purity of the streams provided to the adsorptive zone and/or enhance the purity of the output, such as a raffinate and an extract. Hence, the embodiments disclosed herein can provide a higher purity product and higher recovery of the product.

DEFINITIONS

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As depicted, process flow lines in the figures can be referred to as lines, pipes or streams. Particularly, a line or a pipe can contain one or more streams, and one or more streams can be contained by a line or a pipe. To facilitate understanding, a line may refer to a conduit in a transition zone between an adsorption zone and rotary valve, and a pipe may refer to a conduit outside the transition zone and/or rotary valve.

As used herein, the term "pipe volume" can mean a portion of a pipe that may have a larger diameter than surrounding portions so as to contain a corresponding volume in a line from a transition zone.

As used herein, the term "adsorption" can include adsorption and/or absorption.

As used herein, the term "adsorbent" can include an adsorbent and/or an absorbent, and relates, but is not limited to, adsorption, and/or absorption.

BRIEF DESCRIPTION OF THE DRAWINGS

FIG. 1 is a schematic depiction of an exemplary separation system.

DETAILED DESCRIPTION

The embodiments disclosed herein can be utilized in a variety of adsorptive separation processes. As an example, the embodiments can be utilized for separating para-xylene from a mixture of C8 aromatic isomers, meta-xylene from a mixture of C8 aromatic isomers, linear paraffins from branched and cyclic hydrocarbons, olefins from paraffins, para-cresol or meta-cresol from other cresol isomers, para-cymene or meta-cymene from other cymene isomers, and fructose from mixed sugars. Other applications can include extracting, independently, one or more of the following compounds: monomethyl paraffins, 2,6-dimethyl naphthalene, ethylbenzene, 1-butene, ethyl toluenes, toluidines, terpenes, chloro and nitro aromatics, alpha and beta naphthols, alkyl naphthalenes, alpha olefins, and tall oil, from one or more other compounds. Thus, the embodiments disclosed herein can be used to separate one hydrocarbon from one or more other hydrocarbons.

Typically, the adsorbents can be porous solids. Generally, when the adsorbent is adsorbed in a liquid mixture, the pores fill with liquid, but the equilibrium of distribution of components inside the pores is different from the distribution in the surrounding bulk liquid. The adsorbent can be selective for any component that may be more concentrated inside the pores than surrounding the bulk liquid.

Generally, adsorbents can be classified as polar and nonpolar. A polar or hydrophilic adsorbent can include at least one of a silica gel, an activated aluminum, a silica alumina adsorbent, a molecular sieve and a clay. One exemplary molecular sieve can be a synthetic crystalline zeolite. A wide variety of selectivities can be obtained in such molecular sieves by varying a silica-aluminum ratio, a crystal structure, and cations in the crystal lattice. A nonpolar adsorbent can include at least one of an activated carbon and a coal-derived carbon. Generally, a polar adsorbent is used when the components to be removed are more polar than the bulk process liquid, while a nonpolar adsorbent is used when the target components are less polar.

The embodiments disclosed herein can be utilized with a simulated moving bed using a rotary valve. Typically, a rotary valve switches in steps to facilitate transfer of fluids to and from the adsorption beds. As hereinafter described, valves in a region outside the transition zone can be synchronized with the rotary valve's movements. Such exemplary simulated moving beds are disclosed in, e.g., U.S. Pat. Nos. 3,392,113, 3,617,504, 4,434,051, and 6,407,301 B1.

In these simulated beds, typically a feed and a desorbent are applied at different locations in the bed along with withdrawals of an extract and a raffinate. A circulating adsorbent chamber fluid can simulate a moving bed by changing the composition of the liquid surrounding the adsorbent. Changing the liquid can cause different chemical species to be adsorbed on, and desorbed from, the adsorbent. As an example, initially applying the feed to the adsorbent can result in the desired compound or extract to be adsorbed on the adsorbent, and subsequently applying the desorbent can result in the extract being desorbed and the desorbent being adsorbed. In such a manner, various materials may be extracted from a feed.

Referring to FIG. 1, an exemplary separation system 100 is depicted. The separation system 100 can include an adsorption zone 200, a rotary valve 300, a transition zone 400, and a region 600. The adsorption zone 200 can include an adsorber 210, and a line 220 that can allow the circulation of an adsorbent chamber fluid to simulate a moving bed. Generally, the adsorber 210 can include four beds, namely a first bed 230, a second bed 240, a third bed 250, and a fourth bed 260. Although four beds are disclosed, it should be understood that any number of beds can be used, such as 8, 12, 16, 19, 22, 25, or more.

In addition, a rotary valve 300 is depicted. It should be noted that the rotary valve 300 is depicted in a schematic form to ease depiction of the various stream flows. The rotary valve can be a four-track rotary valve, although other rotary valves can be utilized. In addition, it should be understood that although a rotary valve 300 is depicted, other suitable devices, such as a multivalve manifold arrangement, may be used as well.

The transition zone 400 can include one or more lines such as a plurality of lines 404. Generally, the one or more lines 404 can include a first pair of lines 410, a second pair of lines 420, a third pair of lines 430, and a fourth pair of lines 440. Referring to the first pair of lines 410, generally, the first pair of lines 410 can include a first line 412 having a check valve 414 and a second line 416 having a check valve 418. Correspondingly, the second pair of lines 420 can include a first line 422 having a check valve 424 and a second line 426 having a check valve 428. In addition, the third pair of lines 430 can have a first line 432 having a check valve 434 and a second line 436 having a check valve 438. Moreover, the fourth pair of lines 440 can have a first line 442 having a check valve 444 and a second line 446 having a check valve 448. Generally, the check valves 414, 418, 424, 428, 434, 438, 444, and 448 permit fluid in only one direction, namely toward or away from the adsorption zone 200. Although check valves are disclosed, other unidirectional flow devices may also be used. Particularly, the first lines 412, 422, 432, and 442, of each of the respective pair of lines 410, 420, 430, and 440 can direct fluid in a single direction toward respective beds 230, 240, 250, and 260. Similarly, the second lines 416, 426, 436, and 446 can lead fluid in a single direction away from the respective beds 230, 240, 250, and 260.

The region 600 can include one or more pipes 604 and one or more valves 606 outside the rotary valve 300 and/or the transition zone 400. The one or pipes 604 can include at least one pipe volume 608 corresponding to a volume of one or more lines 404 in the transition zone 400, as hereinafter described. The at least one pipe volume 608 can include a first pipe volume 610, a second pipe volume 630, a third pipe volume 650, and a fourth pipe volume 670. Generally, feed and desorbent streams 504 and 508 can be provided through the one or more pipes 604, namely a pipe 612, and a pipe 632, and raffinate and extract streams 524 and 528 can leave the separation system 100 via a pipe 652 and a pipe 672. Usually, the adsorption zone 200 can receive an input 500 of at least one of the feed stream 504 and the desorbent stream 508 and provide an output 520 of at least one of the raffinate stream 524 and the extract stream 528.

In addition, the one or more valves 606 can control the fluid flow through the region 600. A first control valve 614 and a second control valve 616 can be throttled to regulate the fluid flow in the first pipe volume 610 and in the pipe 612, and a first control valve 634 and a second control valve 636 can be throttled to regulate the fluid flow in the second pipe volume 630 and in the pipe 632. Also, a first control valve 654 and a second control valve 656 can be throttled to regulate the fluid flow in the third pipe volume 650 and in the pipe 652, and a first control valve 674 and a second control valve 676 can be throttled to regulate the flow in the fourth pipe volume 670 and in the pipe 672. These control valves can be flow control valves or be actionable with other process parameters, such as fluid composition.

In addition to the control valves, other sets 620, 640, 660, and 680 of valves can be utilized to control the fluid flow. These sets 620, 640, 660, and 680 can be control valves or global valves, and in this exemplary embodiment they can be global valves. Particularly, a first set of valves 620 can include a first valve 622 and a second valve 624 for regulating the fluid flow in the first pipe volume 610 and the pipe 612; a second set of valves 640 can include a first valve 642 and a second valve 644 for regulating the fluid flow in the second pipe volume 630 and the pipe 632; a third set of valves 660 can include a first valve 662 and a second valve 664 for regulating the fluid flow in the third pipe volume 650 and the pipe 652; and the fourth set of valves 680 can include a first valve 682 and a second valve 684 for regulating the flow in the fourth pipe volume 670 and the pipe 672.

During steady-state operations, the pipe volumes 610 and 630 are used to preload one of the lines 412, 422, 432, or 442, for the next input 500 entering the line. As an example, at the end of the feed cycle, a preload of desorbent is inserted into one of the lines 412, 422, 432, or 442 to be pushed into the adsorption zone 200 at the next desorbent cycle.

Particularly, the feed in the pipe 612 and the raffinate in the pipe 632 can be provided to the rotary valve 300 and to each of the pair of lines 410, 420, 430, and 440, in succession. As a result, the feed, as an example, can pass through the rotary valve 300 through the first line 412 and the check valve 414 to the adsorption bed 230 in the adsorption zone 200. Previous to the embodiments disclosed herein, the first line 412 can contain a remnant from a previous cycle that is not the feed. Generally, it would be preferable to dislodge this remnant to prevent its mixing with the feed in the bed 230. Thus, the second control valve 616 can be throttled to allow desorbent to fill the first pipe volume 610, which initially can contain the feed, and displace feed in the first pipe volume 610 to the pipe 612. During this displacement, the second valve 624 can be closed and the first valve 622 can be opened. The rate of the fluid flow into the pipe 612 can be regulated to allow the desorbent to slowly push the feed that is in the first pipe volume 610 into the pipe 612. At this point, once the first pipe volume 610 fills and the second control valve 616 can be closed, and the feed may pass through the first line 412.

Near the end of the feed cycle, the feed can pass through the first pipe volume 610 by closing the first valve 622 and opening the second valve 624. This pushes the desorbent in the first pipe volume 610 through the second valve 624 and into the first line 412 pushing the desorbent ahead of the feed stream 504. So, at the beginning of the desorbent cycle, the desorbent can push the preloaded desorbent, instead of a feed remnant, in the first line 412 into the first bed 230. Thus, feed contamination of the desorbent cycle can be minimized.

Similarly, the desorbent stream 508 can pass through the pipe 632 and into the rotary valve 300. Subsequently, the desorbent can pass into the first line 422, pass through the one-way check valve 424, and into the second bed 240. During the cycle, the feed can pass through the second control valve 636 and fill the second pipe volume 630 with a feed. While the second pipe volume 630 is being filled, desorbent can be displaced and pushed into the pipe 632. The first control valve 634 can control the normal flow of desorbent in the pipe 632. Once the second pipe volume 630 is filled with feed, the second valve 644 can be opened and the first valve 642 can be closed near the end of the desorbing cycle. The desorbent can push the feed in the second pipe volume 630 into the rotary valve 300 and displace the desorbent in the first line 422. Thus, the feed entering the first line 422 at the beginning of the next feed cycle can push the preloaded feed into the second bed 240. Consequently, the second pipe volume 630 may then be filled with desorbent and when the desorb cycle starts again, the feed can then be allowed back into the second pipe volume 630 to displace the desorbent into the pipe 632.

With respect to the output 520, the raffinate stream 524 and extract stream 528 can be used to fill respective third and fourth pipe volumes 650 and 670 at the beginning of the cycle. As an example, if the raffinate is exiting the first bed 230, the raffinate can pass through the second line 416, pass the check valve 418 to the rotary valve 300. However at the beginning of the cycle, the second line 416 can be filled with extract from the previous cycle. As a consequence, the first valve 662 can be closed and the second valve 664 can be opened allowing the raffinate to push the extract remnant in the second line 416 through the rotary valve 300 through the pipe 652 into the third pipe volume 650. Initially, the third pipe volume 650 can be filled with raffinate from the previous cycle. The extract entering the third pipe volume 650 can push the raffinate into the pipe 652 downstream of the valve 662. Once the third pipe volume 650 is filled with extract, the first valve 662 can open and the second valve 664 can close. At this point, the first and second control valves 654 and 656 can throttle to allow the raffinate in the pipe 652 to push the extract remnant in the third pipe volume 650 past the second control valve 656 where the extract can be withdrawn and combined with the extract stream 528. Once the third pipe volume 650 is cleared of the extract and filled with raffinate, the second control valve 656 can close, and the first control valve 654 can remain open and the raffinate can proceed to the raffinate stream 524. Hence, the third pipe volume 650 is now filled with raffinate at the beginning of the next raffinate cycle.

Similarly, if the extract is being withdrawn from the third bed 250, the previous cycle would have raffinate in the second line 436. Withdrawing the extract from the third bed 250 can dislodge the raffinate in the second line 436 that passes through the check valve 438 and the rotary valve 300. The first valve 682 can close and the second valve 684 can open to force the raffinate in the second line 436 to pass into the fourth pipe volume 670, which may be filled with extract from the previous cycle. Next, the second valve 684 and first control valve 674 can be opened and the first valve 682 and the second control valve 676 can be closed so the raffinate will dislodge the extract in the fourth pipe volume 670 and push it past the second valve 684 and out to the extract stream 528. Once the fourth pipe volume 670 fills with raffinate from the second line 436, the first valve 682 can open and the second valve 684 can close. The first and second control valves 674 and 676 can throttle to allow the extract now passing through the pipe 672 to push the raffinate in the fourth pipe volume 670 past the second control valve 676 to the raffinate stream 524. Once the fourth pipe volume 670 is cleared of the raffinate, the second control valve 676 can close and the first control valve 674 can remain open so that the extract can leave the system through the pipe 672 and exit via the extract stream 528. Hence, the fourth pipe volume 670 can be filled with extract for the next cycle.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A method of minimizing cross-contamination of fluids in a simulated moving bed, comprising:

A) filling a replacement volume on one side of a valve corresponding to a volume in a line on the other side of the valve to either dislodge a remnant of a feed or desorbent in the line from a previous input, or receive a remnant in the line from a previous output wherein the previous input or output is different from the current input or output, wherein the line is a portion of a simulated moving bed adsorption-desorption system with a circulating adsorption chamber fluid comprising an adsorption zone, a rotary valve, and a transition zone with the line is disposed in the transition zone communicating the rotary valve to the adsorption zone.

2. The method according to claim 1, wherein the method dislodges the remnant from a previous input of a feed or a desorbent.

3. The method according to claim 1, wherein the method receives the remnant from an output of a raffinate or an extract.

* * * * *